United States Patent [19]

Kenealy et al.

[11] Patent Number: 5,562,905
[45] Date of Patent: Oct. 8, 1996

[54] HUMAN IMMUNODEFICIENCY VIRUS (HIV) ENV-CODED PEPTIDE CAPABLE OF ELICITING HIV-INHIBITING ANTIBODIES IN MAMMALS

[75] Inventors: William R. Kenealy, Madison, Wis.; Stephen R. Petteway, West Chester, Pa.; Paul J. Durda, Needham, Mass.

[73] Assignee: E. I. Du Pont de Nemours and Company, Wilmington, Del.

[21] Appl. No.: 324,027

[22] Filed: Mar. 20, 1989

Related U.S. Application Data

[63] Continuation-in-part of Ser. No. 186,333, Apr. 26, 1988, abandoned.

[51] Int. Cl.$^6$ .......................... A61K 39/21; A61K 38/00; C07K 5/00; C07K 7/00
[52] U.S. Cl. ...................... 424/188.1; 424/208.1; 530/324; 530/325; 530/326; 530/327
[58] Field of Search ...................... 424/89, 188.1, 424/208.1; 530/324–326, 324, 325, 326, 327

[56] References Cited

U.S. PATENT DOCUMENTS

| | | | |
|---|---|---|---|
| 4,629,783 | 12/1986 | Cosand | 530/324 |
| 5,013,543 | 5/1991 | Haynes et al. | 424/89 |
| 5,019,387 | 5/1991 | Haynes et al. | 424/89 |
| 7,148,692 | of/0000 | Berzofsky et al. | |

FOREIGN PATENT DOCUMENTS

| | | |
|---|---|---|
| 273716 | 7/1988 | European Pat. Off. . |
| 306219 | 3/1989 | European Pat. Off. . |
| 328403 | 8/1989 | European Pat. Off. . |
| 874759 | 7/1987 | South Africa . |
| 2196634 | 5/1988 | United Kingdom . |
| 8702775 | 10/1985 | WIPO . |
| WO87/02775 | 10/1985 | WIPO . |
| 8602383 | 4/1986 | WIPO . |
| 8707616 | 12/1987 | WIPO . |
| 8800471 | 1/1988 | WIPO . |
| 8809181 | 12/1988 | WIPO . |
| 8903391 | 4/1989 | WIPO . |
| 8907112 | 8/1989 | WIPO . |
| 9003984 | 4/1990 | WIPO . |

OTHER PUBLICATIONS

Javaherian, K. et al, Science, vol. 250: 1590–1592, 14 Dec. 1990.
LaRosa, G. et al., Science, vol. 249: 932–935, 24 Aug. 1990.
Ratner, Nature (Jan. 1985) 313: 277–284.
Ho et al, J. of Virol. 61 (1987), 2024–28.
Modrow et al, J. of Virol. 61 (1987), 570–78.
Palker et al., Proc. Natl. Acad. Sci. USA 85:1932–1936 (Mar., 1988).
Rusche et al., Proc. Natl. Acad. Sci. USA 85:3198–3202 (May, 1988).
Goudsmit et al., Proc. Natl. Acad. Sci. USA 85:44784482 (Jun., 1988).
Human Retroviruses and AIDS 1988, Los Alamos National Laboratory, Los Alamos, NM, Nov. 1988.
Gnann, et al., Science 237:1346–1348 (1987).
Norrby, et al., Nature 329:248–250 (1987).

Primary Examiner—Christine M. Nucker
Assistant Examiner—Lynette Smith
Attorney, Agent, or Firm—Blair Q. Ferguson

[57] ABSTRACT

A chemically synthesized 15 amino acid peptide designated peptide 1-69, which has the sequence of amino acids numbers 308 to 322 (RIQRGPGRAFVTIGK) of the human immunodeficiency virus-1 (HIV-1) IIIB env-coded protein, was used to immunize animals. Peptide 1-69 elicited in immunized animals antibodies that block HIV proliferation and block HIV-induced cell fusion in cell culture.

4 Claims, 1 Drawing Sheet

RIQRGPGRAFVTIGK 1-69

HUMAN IMMUNODEFICIENCY VIRUS (HIV) ENV-CODED PEPTIDE CAPABLE OF ELICITING HIV-INHIBITING ANTIBODIES IN MAMMALS

CROSS REFERENCE TO RELATED APPLICATION

This application is a continuation-in-part of U.S. application Ser. No. 07/186,333, filed Apr. 26, 1988, now abandoned.

FIELD OF THE INVENTION

The invention relates to a chemically synthesized peptide corresponding to a segment of the human immunodeficiency virus (HIV) env-coded protein useful as a prophylactic or vaccine for HIV infection and disease, and to monoclonal antibodies to the env-coded segment of HIV.

BACKGROUND

Antibodies specific for human immunodeficiency virus-1 (HIV-1), the causative agent of acquired immunodeficiency syndrome (AIDS), are found in the sera of HIV-infected individuals (Sarngadharan et al. (1984) *Science* 224,506–508; Schupbach et al. (1984) *Science* 224,503–505; Chang et al. (1985) *Biotechnoloy* 3, 905–911; Kenealy et al. (1987) *AIDS Research and Human Retroviruses* 3, 95–105). The level of serum antibodies that block HIV-1 proliferation (HIV-neutralizing antibodies) or block the fusion of HIV-infected and noninfected cells in cell culture (fusion-blocking antibodies) is relatively low when compared to the overall humoral response to the virus (i.e., total levels of HIV-specific antibodies) (Weiss et al. (1985) *Nature* 316,69–74; Robert-Guroff et al. (1985) *Nature* 316, 72–74; Weiss et al. (1986) *Nature* 324,572–575). The role of HIV-neutralizing and fusion-blocking antibodies in the pathogenesis of HIV-1 infection and the structure of the epitopes responsible for this biological activity remain to be determined. The exterior envelope glycoprotein of HIV-1 (gp120) is known to bind human neutralizing antibodies and has been used as an immunogen capable of eliciting HIV-neutralizing antibodies in animals (Lasky et al. (1986) *Science* 233,209–212; Matthews et al. (1986) *Proc. Natl. Acad. Sci. USA* 83,9709–9713; Robey et al. (1986) *Proc. Natl. Acad. Sci. USA* 84,7023–7927). Notably, these neutralizing antibodies are reported to be type-specific, i.e., the antibodies only block proliferation of the HIV-1 subtype or isolate from which the immunogen was derived.

A number of HIV-1 peptides and proteins have been identified which elicit neutralizing antibodies in animals. These include synthetic peptides corresponding to sequences from the gag-coded protein, the env-coded transmembrane protein (gp41), and several peptides corresponding to conserved regions of the env-coded gp120 protein (Putney et al. (1986) *Science* 234,1392–1395; Sarin et al. (1986) *Science* 232,1135–1137; Kennedy et al. (1987) *J. Biol. Chem.* 262,5769–5774; Taylor et al. (1987) *Proc. Natl. Acad. Sci. USA* 84,2951–2955; Chanh et al. (1986) *EMBO J.* 5,3065–3071; Ho et al. (1987) *J. of Virol.* 61,2024–2028). Particularly high levels of neutralizing and fusion-blocking antibodies have been shown to be induced in animals by two recombinant proteins. One of these is a glycosylated full length env-coded protein produced using an insect cell expression system, designated gp160 (Rusche et al. (1987) *Proc. Natl. Acad. Sci. USA* 84,6924–6928) and a second is a nonglycosylated *Escherichia coli* produced protein, designated PB1, representing a region of gp120 (amino acids number 288 to 472 of HIV-1 IIIB) (Putney et al. (1986) *Science* 234,1392–1395). In spite of the strong antibody responses using these proteins as immunogens, the neutralizing activity remained restricted to and specific for the HIV-1 subtype or isolate from which the immunogen was derived, i.e., IIIB.

Recombinant proteins PE3 (corresponding to the amino terminus of the env-coded gp120) and ENV9 (corresponding to the carboxyl-terminus of gp120 and most of gp41) did not elicit measurable levels of neutralizing activity (Putney et al. (1986) *Science* 234,1392–1395), whereas PB1 was capable of inducing levels of neutralizing and fusion-blocking antibodies comparable to or greater than those elicited using the recombinant gp160 (Rusche et al. (1987) *Proc. Natl. Acad. Sci. USA* 84,6924–6928).

SUMMARY OF THE INVENTION

*E. coil*-expressed HIV-1env-derived protein PB1 is known, when used as an immunogen, to elicit high levels of neutralizing and fusion-blocking antibodies in animals (Puthey et al. (1986) *Science* 234,1392–1395). Such an immune response in animals suggests that this region of HIV env may be useful for therapy for or prevention of HIV infection and disease. We have undertaken a systematic analysis to further define segments within the PB1 region of gp120 that may be involved in the neutralizing and fusion-blocking activity. A systematic analysis, using a series of overlapping chemically synthesized peptides which represent the entire PB1 region (amino acids number 288 to 472 of HIV-1 IIIB env-coded protein gp120) was employed. The peptides were between 15 and 16 amino acids in length and overlapped one another by five amino acids. These synthetic peptides were used to immunize test animals (guinea pig) and the resultant anti-peptide antibodies produced in the test animals were analyzed for biological activity, including HIV-neutralizing and cell fusion-blocking activity.

The synthetic peptides spanning the HIV-1 env-coded PB1 region that were analyzed are listed in Table 1. Of the 18 peptides tested, only one peptide, designated 1-69, when used as an immunogen, elicited antibodies that blocked both HIV proliferation in cell culture and the fusion between HIV-infected and noninfected cells in cell culture. This finding indicates that peptide 1-69 or peptides of about the same length (10 to 30 amino acids or, more preferably, 15 to 25 amino acids) encompassing most of the sequence of peptide 1-69 may be useful as a prophylactic or vaccine for HIV infection, or as a component of a prophylactic or vaccine for HIV infection. Smaller peptides of 5 to 10 amino acids encompassing part of the sequence of peptide 1-69 are expected to be useful for inducing HIV-inhibiting antibodies in a mammal. Useful peptides include QRGPGRA, RIQRGPGRA, GPGRAFVTIG, GPGRAFV, and GPGRA. Somewhat larger peptides of about 36 aa length, and extending from HIV-1 IIIB env-coded Cys 296 to Cys 331 (see Table 4) and encompassing peptide 1-69, are also expected to elicit HIV-inhibiting antibodies in animals.

Antibodies which inhibit HIV proliferation and block HIV-mediated cell fusion are likely to provide increased resistance to HIV infection. As used herein, the term "HIV-inhibiting antibodies" includes both neutralizing and fusion-blocking antibodies. The ability to detect the presence or absence of such HIV-inhibiting antibodies in patients may have important prognostic value. Pharmaceutical preparations containing such antibodies could be used for passive immunization of individuals exposed to HIV. Moreover, such antibodies are likely to reduce the rate of disease progression to AIDS in HIV-infected individuals as well as having potential therapeutic value in AIDS patients. Monoclonal HIV-inhibiting antibodies of the invention are expected to be particularly useful.

The HIV-neutralizing and fusion-blocking activities of anti-peptide 1-69 antibodies appear to be largely restricted to the HIV isolate from which the peptide sequence was derived since HIV-1 IIIB was inhibited but HIV-1 RF was not. However, the env-coded region homologous to HIV-1 IIIB peptide 1-69 from other isolates of HIV can be readily identified by amino acid sequence comparison (Table 4), and the corresponding peptides can be synthesized and used as immunogens using the procedures described for peptide 1-69. Moreover, inhibition of HIV-1 subtypes or isolates having closely related sequences in the region of amino acid number 296-331 of gp120 would be expected. Indeed, MAb #5025,29.1.1.1 (ATCC #HB10041) exhibits fusion blocking activity against a number of HIV-1 isolates, such as IIIB and MN.

The term "corresponding to", as used herein in reference to amino acid (aa) sequences, refers to the relationship between aa which are aligned with one another when two or more aa sequences are compared and aligned for homology using standard computer programs, such as those available from, for example, IntelliGenetics, Inc., Mountain View, Calif. or Genetics Computer Group, University of Wisconsin Biotechnology Center, Madison, Wis.

The sequences of env-coded peptides for different HIV-1 and HIV-2 isolates, corresponding to the region homologous to HIV-1 IIIB peptide 1-69, are listed in Table 4. The env-coded region corresponding to HIV-1 IIIB peptide 1-69 can be identified using procedures as described in the legend of Table 4. Although the envelope proteins from different HIV isolates have regions of considerable variability in aa sequence, the overall structure of the protein, including, for example, the relative position of Cys residues (see Table 4), is well conserved. Since the overall structure and functional properties (for example, CD4 binding) of the env proteins from different HIV isolates are well conserved, the env-coded regions corresponding to peptide 1-69 from other HIV-1 and HIV-2 isolates are expected to similarly elicit HIV-neutralizing and cell fusion-blocking antibodies in animals immunized with the peptide. Effective vaccines or prophylactics for HIV infection may comprise a mixture or "cocktail" of peptides which include regions corresponding to HIV-1IIIB peptide 1-69. Preferably such a mixture would include peptides corresponding to peptide 1-69, or somewhat larger or smaller equivalent peptides, from a variety of HIV-1 isolates. Such a mixture or "cocktail" would potentially confer broad resistance to many distinct isolates of HIV.

This invention also relates to HIV-inhibiting monoclonal antibodies to the HIV-1 envelope-derived peptide 1-69. In particular, a series of murine monoclonal antibodies were raised to the synthetic HIV-envelope-derived peptide designated 1-69. One of these murine monoclonal antibodies, known by its hybridoma clone #5023,24.4.1.1 (ATCC #HB10043), has been shown to have particularly strong HIV-1 virus neutralizing activity against the IIIB isolate and to block the fusion of HIV-1 IIIB infected cells with uninfected target cells. Another of these MAbs, #5025,29.1.1.1 (ATCC #HB10041), has been shown to have fusion blocking activity against a number of HIV-1 isolates.

DETAILED DESCRIPTION

Figure 1:
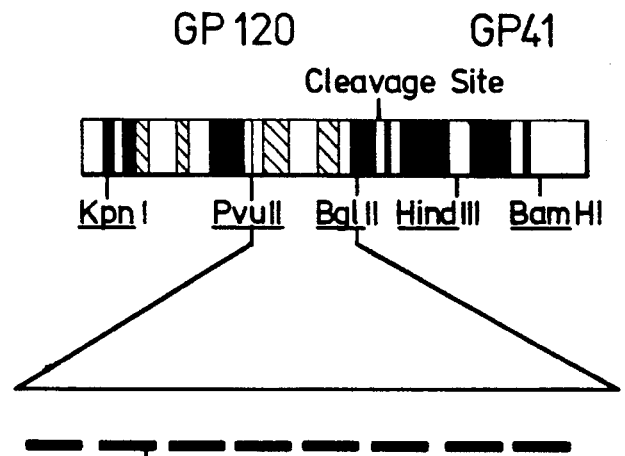

An *E. coli*-produced protein designated PB1, which encompasses HIV-1 IIIB env-coded amino acids number 288 to 472, has been shown previously to elicit antibodies with HIV-neutralizing and fusion-blocking activities in immunized animals (Putney et al. (1986) *Science* 234, 1392–1395). We systematically analyzed the antigenic and immunogenic properties of a set of 18 overlapping synthetic peptides (Table 1) completely spanning the entire PB1 region in an attempt to define epitopes that may elicit antibodies with HIV-neutralizing and cell fusion-blocking activities.

The peptides were analyzed as antigens to determine whether they were recognized by antibodies from human HIV-1 seropositive serum samples (Table 1). This analysis revealed two peptides, designated 1-69 and 1-73, which were reactive with many HIV-1 seropositive serum samples when compared to the nonspecific binding of antibodies to microtiter plates. The reactivity of several of the env-coded peptides with human antibodies in HIV-1 seropositive serum samples was further analyzed and compared to that of control HIV-1 seronegative serum samples (Table 2). Peptide 1-69 gave high levels of reactivity with 12 of 37 of the HIV-1 seropositive serum samples tested, whereas none of the 47 control HIV-1 seronegative serum samples tested had ELISA absorbances above the cutoff value of 0.2. The frequency of reactivity and the level of reactivity of HIV-seropositive serum samples with peptides 1-80 and 1-73 were lower than with peptide 1-69. There was some reactivity (3 of 47 serum samples tested) of control sera with peptide 1-73. There is a clear correlation of serum sample reactivity with peptides 1-69 and 1-80, and HIV-1 seropositivity, i.e., ELISAs utilizing peptide 1-69 or peptide 1-80 show specificity for HIV-specific antibodies. Peptides 1-69 and 1-80, and the corresponding peptides from other HIV isolates, are useful for the detection of HIV-specific antibodies in human serum samples for diagnostic or prognostic purposes. Peptide 1-80 comprises aa number 418 to 432 of HIV-1 IIIB env-coded protein. Peptide 1-69 comprises aa number 308 to 322 of HIV-1 IIIB env-coded protein. Under the conditions used in Table 2, peptides 1-68, 1-74, 1-77, 1-81 and 1-84 were detected by very few HIV-1 seropositive samples ($\leq 1$ per 37 samples tested). The differences in the ELISA absorbance values and the frequency of positively reactive serum samples for a given peptide in Table 1 and 2 (for example, peptide 1-81, 1-84, 1-73), probably reflects differences in the conditions used in Table 1 and 2.

When the immunogenicity of the peptides was investigated (Table 3), it was found that five of the peptides (1–67, 1–75, 1–77, 1–80, and 1–83) were unable to elicit a high anti-peptide antibody titer in guinea pigs. Of the guinea pig serum samples that had significant levels of anti-peptide antibodies, only those elicited to peptide 1-69 had the following detectable activities: 1) reactive with env-coded gp120 on immunoblots (Table 3); 2) able to immunoprecipitate gp120 (data not shown); 3) able to neutralize HIV-1 IIIB proliferation in cell culture (Table 3); 4) able to block cell fusion between HIV-1 IIIB infected and noninfected cells in cell culture (Table 3).

When using a virus neutralization test, the antipeptide 1-69 sera gave a 50% inhibition at 1:300 dilution. This level of neutralizing activity is equal to or greater than that previously reported for antibodies to gp120 purified from HIV-infected cells or recombinant env-derived proteins or any chemically synthesized HIV-derived peptides (Lasky et al. (1986) *Science* 233,209–212; Matthews et al. (1986) *Proc. Natl. Acad. Sci. USA* 83,9709–9713; Taylor et al. (1987) *Proc. Natl. Acad. Sci. USA* 84,2951–2955; Chanh et al. (1986) *EMBO J.* 5,3065–3071; Ho et al. (1987) *J. of Virol* 61,2024–2028). It is remarkable and of interest that a small chemically synthesized peptide sequence from a complex highly glycosylated protein such as gp120 is capable of eliciting an apparently stronger neutralizing response than the native protein. It appears that an inappropriate immunological response may preempt a protective response. It is possible that antibodies specific to other regions of env, outside the peptide 1-69 region, interfere with the binding of neutralizing antibodies specific for the peptide 1-69 region of env. It is also possible that other encoded epitopes, outside the peptide 1-69 region, interfere with a strong immune response specific for the peptide 1-69 region of env. It is known that antibody attached to free virus is more likely to bind to macrophages, thereby increasing the likelihood of macrophages becoming infected. These considerations could explain why peptide 1-69 is a better immunogen than larger segments of env protein, in terms of ability to elicit in animals HIV-inhibiting antibodies. Thus, the use of an appropriate peptide immunogen avoids eliciting HIV-specific antibodies in an animal that have no protective function.

Furthermore, the anti-peptide 1-69 sera were able to block cell fusion, a property not exhibited by goat antibodies specific to gp120 purified from HIV-infected cells (Matthews et al. (1986) *Proc. Natl. Sci. USA* 83,9709–9713). The level of fusion-blocking antibodies in anti-peptide 1-69 sera are comparable to the highest levels found in HIV-1 seropositive sera (Matthews et al. (1987) *Proc. Natl. Acad. Sci. USA* 84,424–5428).

The anti-peptide 1-69 sera only neutralized HIV-1 IIIB and blocked fusion of HIV-1IIIB-infected cells and did not have any effect on HIV-1RF. Hahn et al. and others (Hahn et al. (1985) *Proc. Natl. Acad. USA* 82,4813–4817; Starcich et al. (1986) *Cell* 45,637–648; Hahn et al. (1986) *Science* 232,1548–1553) identified regions of predicted amino acid variability within the gp120 protein and predicted that the type or isolate specificity of antiviral antibodies is due to recognition of these hypervariable regions. Our results identify a potent neutralizing and fusion-blocking region comprising 15 amino acids within one of the predicted hypervariable regions and support the role of amino acid variation in type or isolate restricted neutralization. The reactivity of HIV-1 positive sera with this same peptide indicates that this protein region is recognized and elicits antibodies during HIV-1 infection.

Computer derived predictions of antigenic regions for gp120 were reported by Modrow et al. (Modrow et al. (1987) *J. of Virol.* 61,570–578). The region covered by peptide 1-69 is within one of the regions predicted to be antigenic for the HIV-1 IIIB isolate. A portion of the peptide 1-73 is also predicted to be antigenic, but the other peptide reactive with HIV-1 positive sera, 1-80 was not. The reactivity to peptide 1-80 merits further examination since this peptide is derived from a conserved region of gp120. Thus, peptide 1-80 should be useful for the detection of human antibodies elicited in response to many distinct HIV isolates, whose env-coded proteins may differ in sequence in regions not within the conserved region.

Although the HIV-inhibiting activity of the anti-peptide 1-69 sera appears to be specific for the IIIB isolate, it is of interest that the antibodies which mediate neutralization and block cell fusion are made in response to a single short (15 amino acid) peptide sequence. This result suggests that there may be a common mechanism of virus neutralization and cell fusion inhibition, since the same 15 aa region of env appears to be critical for both processes. HIV envelope proteins have been shown previously to play a role in both viral infectivity and the fusion of infected cells, and certain human and animal antibodies specific for env-derived proteins block both virus infectivity and fusion (Putney et al. (1986) *Science* 234,1392–1395; Rusche et al. (1987) *Proc. Natl. Acad. Sci. USA* 84,6924–6928). Our results demonstrate that antibodies responsible for both activities can bind within a single 15 amino acid region of gp120. Surprisingly, monoclonal antibodies of the invention have been shown to exhibit both HIV-neutralization and fusion blocking activities. Binding of the anti-peptide 1-69 antibody to this region could also interfere with the interaction of gp120 and gp41, although other possible mechanisms of HIV-inhibition by anti-peptide 1-69 are possible.

Monoclonal antibodies that neutralize virus and block the fusion of infected and uninfected cells may provide increased resistance against HIV-1 infection while avoiding an inappropriate and potentially harmful immunological response.

Monoclonal antibodies to peptide 1-69 or to corresponding segments of envelope protein from other HIV-1 isolates could be used to provide passive immunity or therapeutic benefit to patients exposed to or infected with an AIDS virus, as research reagents, or as reagents to develop anti-idiotypic antibodies. Anti-idiotypic antibodies can be used as immunogens to develop immunity to the antigen to which the original antibody Ab1 was raised. In the case of HIV infection immunization with anti-idiotypic antibodies would provide a safe alternative to immunization with whole virus or with vital components.

A series of murine monoclonal antibodies to the synthetic peptide 1-69 were developed. One of these monoclonal antibodies known by its hybridoma clone #5023,24.4.1.1 (ATCC #HB10043) has been shown to have particularly strong HIV-1 virus neutralizing activity against the IIIB isolate and to block the fusion of HIV-1 IIIB infected cells with uninfected target cells. As such it would be expected to be useful for providing passive immunity in patients exposed to the HIV-1 IIIB isolate, or as a therapeutic agent to slow the course of the disease in patients infected with the virus. MAb #5023,24.4.1.1 also showed strong Western blotting activity towards env gp120, which suggests its potential utility for diagnostic purposes. These monoclonal antibodies would also be prime reagents to be used to develop anti-idiotypic antibodies for vaccine production. Other MAbs raised to this same peptide have lower levels of neutralizing activity; these will also be described below.

Tables 1 and 4 list amino acid (aa) sequences of peptides using single letter symbols to represent aa residues, as described in Lehninger, *Biochemistry*, 2nd Edition, p. 72, Worth Publishers, Inc. (1975). Accordingly, the aa sequence of peptide 1-69 can be identified as RIQRGPGRAFVTIGK or Arg-Ile-Gln-Arg-Gly-Pro-Gly-Arg-Ala-Phe-Val-Thr-Ile-Gly-Lys.

A valuable source of information about various pharmaceutical formulations and dosage forms is *Remingtion's Pharmceutical Sciences*, 17th Edition (1985), Mack Publishing Company, Easton, Pa. 18042.

FIGURE LEGENDS

FIG. 1

Map of the HIV-1env-coding sequence covered by overlapping synthetic peptides. Solid areas represent conserved protein regions and shaded areas are hypervariable regions (Puthey et al. (1986) *Science* 234,1392–1395; Satin et al. (1986) *Science* 232,1135–1137).

FIG. 2

Immunoreactivity in solid phase ELISA of various MAbs with peptides 1-69 (the immunizing peptide), 1-178, 1-177, 5, 1-68, and 1-70. The sequences of these peptides are shown in Table 6.

MATERIALS AND METHODS

Synthesis and Characterization of Peptides

Overlapping peptides were made using the Rapid Multiple Peptide Synthesis System (RAMPS, E. I. du Pont de Nemours and Company, Wilmington, Del.). This system utilizes solid phase FMOC chemistry in a manual format. The solid supports were p-alkoxybenzyl alcohol resins from Bachem Inc. (Torrance, Calif.). Amine substitutions on the resins ranged from approximately 0.25 to 0.65 mmol/g. Pentafluorophenyl esters of the protected amino acids (Milligen, Bedford, Mass.) were used for the primary activation strategy, with hydroxybenzotriazole assisted or preformed symmetric anhydrides reserved as alternate strategies. The coupling efficiencies were monitored qualitatively by ninhydrin (Kaiser test) or isatin for residues added to prolines. Both tests detected unreacted amine groups. By allowing each coupling to react until a negative Kaiser or isatin test is achieved, coupling efficiencies of >99% can be obtained. Cleavage of the peptidyl resins by acid hydrolysis gave peptides with free carboxyl groups at their C-termini. These peptides were first characterized to batch consistency by reverse phase chromatography on a Pharmacia FPLC Pep-RPC HR5/5 column using a 20 to 80% acetonitrile:water gradient. All peptides were further analyzed by fast atom bombardment-mass spectrometry. The intended sequence of a given peptide was inferred to be present if a major ion of the calculated M+H was apparent. Those peptides showing either no distinguishable major peak by FPLC or no molecular ion of mass M+H were rejected and resynthesized.

Enzyme-Linked Immunosorbent Assay (ELISA) Detection of the Binding of Antibodies to Peptides Synthetic peptides were immobilized directly on Immulon®-II microtiter plates using glutaraldehyde. The plates were activated with 2% glutaraldehyde for 2 hrs at room temperature or 0.1% glutaraldehyde for 30 min and rinsed with deionized water. Two conditions of glutaraldehyde treatment were used routinely; the 2% glutaraldehyde was used to ensure adequate binding of the peptide to the plate and the 0.1% glutaraldehyde to avoid alteration of the binding sites. Peptide solutions of 100 µl containing 10 µg/ml in 60 mM bicarbonate buffer, pH 9.6, were added per well and incubated overnight at 4° C. The plates were washed and blocked with PBST (phosphate buffered saline +0.05% Tween® 10) for 1 hr at 37° C. and stored dry at 4° C.

Peptides that did not react with HIV seropositive sera when coupled directly to the microtiter plate well using the glutaraldehyde procedure above were also conjugated to human serum albumin (HSA) as described below. This procedure was used to assure immobilization of the peptide to the microtiter plate. The peptide-HSA conjugate was immobilized on the microtiter plate well using the procedure above, except that glutaraldehyde was not included in the reaction.

Immediately before use, where indicated, the plates were blocked again with 100 µl of diluent (PBST +5% bovine serum albumin +20% heat inactivated normal goat serum +0.1% sodium azide +0.05% thimerosal) for 30 to 60 min at 37° C. Human serum samples diluted 1:20 with the diluent (100 µl) were added to each well and incubated for 2 hrs at room temperature. Incubation with the alkaline phosphatase-conjugated goat anti-human IgG (Jackson Immunoresearch Laboratories, Avondale, Pa.) was carried out for 1 hr at room temperature and the color developed for 1 hr at room temperature using o-nitrophenol phosphate as substrate. The optical density or absorbance of the reaction was determined using a microtiter plate reader.

Conjugation of Peptides to Protein Carriers

Peptides were conjugated to either ovalbumin or keyhole limpet hemocyanin prior to immunization. For ELISA studies, human serum albumin (HSA) was used as the carrier protein. Carrier protein (2 mg/ml) was activated with 0.5% glutaraldehyde for 30 to 60 min at room temperature, then an equal volume of the peptide solution (2 mg/ml in dimethylsulfoxide) was added. The reaction took place overnight at 4° C., following which the reaction mixture was dialyzed overnight against deionized water or 0.1M glycine, pH 7.0 in the case of human serum albumin.

Immunization Procedures

Guinea pigs and rabbits were immunized following standard immunization protocols. Guinea pigs and rabbits were immunized initially with 100 to 200 µg of the peptide-carrier protein conjugate in complete Freund's adjuvant, and boosted using half the amount of peptide-carrier protein conjugate in incomplete Freund's adjuvant every two weeks thereafter. Serum samples were obtained at every other boost.

HIV Neutralization and Cell Fusion Assays

Approximately 500 $TCID_{50}$ infectious units of HIV-1 IIIB or HIV-1 RF in 25 µl were mixed and incubated with serum dilutions (25 µl) for 30 min at 37° C. Molt 4 cells ($4 \times 10_4$) were added in a volume of 100 µl and incubation continued for six days at 37° C. The final dilution of the serum sample was 1 to 20. The total volume of each culture was doubled daily by addition of fresh medium (RPMI+20% fetal calf serum). On day six, 100 µl samples were taken from the supernatant and tested for the level of viral gag-coded p24 antigen using an antigen capture assay (Du Pont, Wilmington, Del.).

The cell fusion assay has been described (Matthews et al. (1987) *Proc. Natl. Acad. Sci. USA* 84,424–5428). Briefly, 5000 CEM cells chronically infected with HIV-1 IIIB or HIV-1RF were mixed with 75,000 Molt 4 cells in a volume of 100 µl in a 96 well half-area plate. Final dilution of sera in the assay was 1 to 20. Twenty-four hours later giant cells were visually enumerated at a 40× magnification.

Radio immunoprecipitation

Culture media (3 ml), from $8 \times 10^6$ cells labeled with 500 µCi each methionine ($^{35}S$, 600 µCi/mmol) and cysteine ($^{35}S$, 600 µCi/mmol) for 4 hrs, were used for the assay. The culture media was preadsorbed with normal human serum and protein A-Sepharose. Proteins were immunoprecipitated using human HIV-1 positive serum or guinea pig serum samples and protein A-Sepharose. Proteins were separated by a $NaDodSO_4$-PAGE (10%) and the gel was autoradiographed.

EXAMPLES

Example 1

Binding of Human Antibodies to Chemically Synthesized Peptides Corresponding to HIV-1 IIIB env Peptides were synthesized as described in the Material and Methods. This procedure allowed the synthesis of peptides in sufficient quantities to screen for human antibody reactivity and for the immunization of animals. The region covered by the peptides is outlined in FIG. 1 and includes the sequences of the PB1 recombinant protein (Putney et al. (1986) *Science* 234,1392–1395). The peptides were designed with a 5 amino acid overlap so that any sequence of 6 consecutive amino acids would be represented.

All the peptides shown in Table 1 were assayed for reactivity with 12 human HIV-1 seropositive serum samples, i.e., recognition of the peptide by human HIV-specific antibodies. Table 1 shows the number of serum samples for any given peptide which had an average ELISA absorbance 5-fold greater than the background absorbance obtained with the serum sample using glutaraldehyde treated blank wells not containing peptide. Table 1 shows data obtained using 2% glutaraldehyde in the procedure for coupling. The ELISA absorbances were highest for the peptides 1-69 and 1-73 and these peptides also had the highest percentage of serum samples reacting with them. The following peptides are scored as reactive using an ELISA absorbance cut-off of 10-fold greater than the background absorbance obtained with control wells not containing peptide (peptide designation/number of positive sera): 1-69/5, 1-72/1, 1-73/3, 1-74/2, 1-77/1, 1-78/1, 1-81/2, 1-83/1, and 1-84/1.

When 0.1% glutaraldehyde was used in the procedure for peptide attachment, the background ELISA absorbances were lower. In this analysis, the only peptide which had absorbances 5-fold greater than the background was peptide 1-69. Nine of 12 serum samples were reactive with peptide 1-69 with an average absorbance of 1.06±0.47. If an ELISA absorbance cutoff of 10-fold greater than the background was used, 6 of 12 serum samples were scored as positive with peptide 1-69, using the 0.1% glutaraldehyde procedure for peptide attachment.

In addition, peptides 1-67, 1-70, 1-71, 1-75, 1-76, and 1-79, which did not appear to bind to human antibodies in the experiment of Table 1, were tested using a third technique for peptide immobilization on the microtiter plate. These peptides were first conjugated to human serum albumin (HSA) and then the peptide-HSA conjugate was immobilized on the microtiter plate and tested for reactivity with HIV-1 positive human serum samples by ELISA. These peptide conjugates still did not give ELISA absorbances significantly above the control sera.

Thirty-seven HIV-1 seropositive serum samples and 49 normal HIV-1 seronegative serum samples were analyzed using selected peptide ELISAs and the results are shown in Table 2. Three normal serum samples gave ELISA absorbances above the cutoff using peptide 1-73. None of the normal HIV-1 seronegative serum samples were positive using peptides 1-69 or 1-80 in the ELISA. Of the 37 HIV-1 seropositive serum samples tested, 12 were positive using peptide 1-69 in the ELISA, 16 were positive using peptide 1-73 in the ELISA, and 14 were positive using peptide 1-80 in the ELISA. The HIV-1 positive serum samples were more reactive with peptide 1-69 as compared with 1-73 and 1-80, based on the average ELISA absorbance values. The high standard deviation and low mean for peptide 1-73 indicates that many of the HIV-1 positive serum samples are no more reactive with this peptide than are some normal serum samples; on the other hand, the high standard deviation for 1-69 and 1-80 is representative of a wide range in reactivity from serum to serum.

Peptide 1-69 is derived from one of the hypervariable regions of the env-coded gp120 protein (Modrow et al. (1987) *J. of Virol.* 61,570–578) (Table 4), whereas peptides 1-73 and 1-80 were derived from less variable regions that have some conservation of sequence among different isolates of the virus (Modrow et al. (1987) *J. of Virol.* 61,570–578). Given that peptide 1-69 is derived from a hypervariable region, it is surprising that a relatively high percentage of the HIV-1 seropositive serum samples tested positive using the peptide 1-69 ELISA. It is possible that much of the immunoreactivity is specific for the highly conserved Gly-Pro-Gly sequence within peptide 1-69. The ELISA absorbance values obtained using peptide 1-69 with HIV-1 positive sera is on the average greater than 1-73 and 1-80, however, the assays with these peptides have not been optimized. The lower ELISA absorbances for serum samples with peptide 1-73 as shown in Table 2 as compared to Table 1 is a result of the incubation of the plates with diluent prior to serum exposure.

Example 2

Synthetic Peptides Corresponding to HIV-1 IIIB env as Immunogens

All of the peptides listed in Table 1 were conjugated to a carrier protein (either keyhole limpet hemocyanin or ovalbumin) and each peptide-carrier protein conjugate was used to immunize two guinea pigs. Guinea pigs were selected as a convenient test animal system. The resultant guinea pig antiserum samples were monitored for anti-peptide reactivity using ELISA procedures. Peptide 1-76 was injected initially into guinea pigs but the animals succumbed soon after the initial injection. The peptide was then injected into rabbits where anti-peptide antibodies were elicited without adverse effects. A time point of six months was selected for testing the antiviral (i.e, HIV neutralizing and cell fusion-blocking) characteristics of the guinea pig antisera.

The data in Table 3 show that most of the peptides induced the production of peptide-specific antibodies by 6 months following the first immunization. Although different levels of antibodies were produced, there was no case where only one animal from the pair produced antibodies. Peptides 1-67, 1-75, 1-77, 1-80, and 1-83 elicited very low levels of anti-peptide antibodies under the conditions used for conjugation and immunization. Animals which produced significant levels of anti-peptide antibodies usually showed reactivity by the third month and the level increased for the next 2 to 3 months.

The only anti-peptide serum samples which bound to gp120 on immunoblot strips were anti-peptide 1-69; they showed clear reactivity with only the 120/160 bands of HIV-1 IIIB (data not shown). Anti-peptide 1-69 serum samples were also the only serum samples from these experiments which were able to radioimmunoprecipitate gp120 from strain HIV-1 IIIB (data not shown). When assayed by immunoblot using recombinant *Escherichia coli*-produced protein ENV-14 (ENV-14 encompasses amino acids 40-511 of HIV-1 IIIB), which encompasses the region of gp120 from which the peptides are derived, reactivity was detected only with antisera specific for peptides 1-68, 1-69, 1-76, and 1-82. All of these peptides except 1-69 contain potential glycosylation sites. It is possible that glycosylation of gp120 in mammalian cells prevents binding of antibodies specific for (the unglycosylated) peptides 1-68, 1-76, and 1-82.

The guinea pig serum samples were also tested for the ability to inhibit HIV proliferation, i.e., to neutralize HIV, and to block cell fusion between HIV-infected and non-infected cells, in cell culture (Table 3). The only serum samples which were able to neutralize HIV-1 IIIB and block fusion were those raised against peptide 1-69. Both neutralizing and fusion blocking activities are indicated to be type specific, since HIV-1 IIIB was neutralized by anti-peptide 1-69 antibodies, whereas HIV-1 RF was not. The same was true for the blocking of cell fusion.

As shown in Table 5, the appearance of detectable HIV cell fusion-blocking antibodies in animals immunized with peptide 1-69 did not occur until 5 months following the start of the immunization; the maximum antibody titer for this activity was obtained at 6 months following start of the immunization.

TABLE 1

ELISA reactivity of HIV-1 seropositive serum samples with peptides corresponding to HIV-1 IIIB env-coded amino acid sequences

| Number | PEPTIDE Sequence | Number of Peptide ELISA Positive Sera of 12 Tested | Positive Sera Average Absorbance ± SD |
|---|---|---|---|
| 1-67 | LNQSVGINCTRPNNNT | 0 | — |
| 1-68 | RPNNNTRKSIRIQRG | 1 | 0.23 ± 0.00 |
| 1-69 | RIQRGPGRAFVTIGK | 8 | 0.79 ± 0.40 |
| 1-70 | VTIGKIGNMRQAHCNI | 0 | — |
| 1-71 | QAHCNISRAKWNNTL | 0 | — |
| 1-72 | WNNTLKQIDSKLREQF | 4 | 0.29 ± 0.10 |
| 1-73 | KLREQFGNNKTIIFK | 10 | 0.85 ± 0.44 |

TABLE 1-continued

ELISA reactivity of HIV-1 seropositive serum samples with peptides corresponding to HIV-1 IIIB env-coded amino acid sequences

| Number | PEPTIDE Sequence | Number of Peptide ELISA Positive Sera of 12 Tested | Positive Sera Average Absorbance ± SD |
|---|---|---|---|
| 1-74 | TIIFKQSSGGDPEIV | 4 | 0.34 ± 0.10 |
| 1-75 | DPEIVTHSFNCGGEF | 0 | — |
| 1-76 | CGGEFFYCNSTQLFNS | 0 | — |
| 1-77 | TQLFNSTWFDSTWST | 5 | 0.36 ± 0.13 |
| 1-78 | STWSTKGSNNTEGSD | 4 | 0.30 ± 0.12 |
| 1-79 | TEGSATITLPCRIKQI | 0 | — |
| 1-80 | CRIKQIINMWQEVGK | 2 | 0.22 ± 0.06 |
| 1-81 | QEVGKAMYAPPISGQI | 5 | 0.37 ± 0.10 |
| 1-82 | PISGQIRCSSNITGL | 1 | 0.21 ± 0.02 |
| 1-83 | NITGLLLTRDGGNSNE | 3 | 0.29 ± 0.06 |
| 1-84 | GGNSNNESEIFRPGG | 5 | 0.31 ± 0.06 |

ELISAs were run as described in the Materials and Methods using the 2% glutaraldehyde procedure for attachment to the plates. The sera were scored as positive if they gave an ELISA absorbance in the peptide assay 5-fold greater than glutaraldehyde treated control wells not containing peptide. The average absorbances and standard deviation were calculated using all of the determinations for the reactive sera (duplicate wells for each sera). Twelve HIV-1 seropositive serum samples were tested.

TABLE 2

Comparison of the reactivity of human HIV-1 seropositive and seronegative serum samples on selected peptide ELISAs.

| | HIV SEROPOSITIVE SERA | | NORMAL SERONEGATIVE SERA | |
|---|---|---|---|---|
| PEPTIDE Number | Number of Peptide ELISA Positive Sera of 37 Tested | Positive Sera Average Absorbance ± SD | Number of Peptide ELISA Positive Sera of 47 Tested | Positive Sera Average Absorbance ± SD |
| 1-68 | 1 | 0.21 ; 0.00 | 0 | — |
| 1-69 | 12 | 0.71 ± 0.49 | 0 | — |
| 1-73 | 16 | 0.28 ± 0.13 | 3 | 0.24 ± 0.03 |
| 1-74 | 0 | — | 0 | — |
| 1-77 | 0 | — | 0 | — |
| 1-80 | 14 | 0.34 ± 0.24 | 0 | — |
| 1-81 | 1 | 0.21 ; 0.00 | 0 | — |
| 1-84 | 0 | — | 0 | — |

ELISAs were run as in Table 1 except the microtiter wells were blocked with diluent for 1 hour prior to use. Serum samples were scored as positive if they gave an ELISA absorbance greater than 0.2. 37 HIV-1 positive serum samples and 47 normal serum samples were tested.

TABLE 3

Characterization and assessment of antiviral activity of antibodies elicited by peptides.

| PEPTIDE* | LIMITING + DILUTION | FUSION** ASSAY | NEUTRALIZATION# ACTIVITY | IMMUNOBLOT | |
|---|---|---|---|---|---|
| | | | | gp120 | env 14 |
| 1-67 | <20 | 59,ND | >800 | — | — |
| 1-67 | <20 | 69,65 | >800 | — | — |
| 1-68 | 4000 | 70,78 | >800 | — | + |
| 1-68 | 870 | 88,60 | >800 | — | + |
| 1-69 | 5000 | 3,0 | <1.5 | + | + |

TABLE 3-continued

Characterization and assessment of antiviral activity of antibodies elicited by peptides.

| PEPTIDE* | LIMITING +<br>DILUTION | FUSION**<br>ASSAY | NEUTRALIZATION#<br>ACTIVITY | IMMUNOBLOT gp120 | IMMUNOBLOT env 14 |
|---|---|---|---|---|---|
| 1-69 | 970 | 0,0 | <1.5 | + | + |
| 1-70 | 1650 | 66,71 | 800 | − | − |
| 1-70 | 80 | 68,58 | >800 | − | − |
| 1-71 | 3030 | 63,48 | >800 | − | − |
| 1-71 | 5310 | 72,72 | >800 | − | − |
| 1-72 | 1050 | 68,65 | >800 | − | − |
| 1-72 | 660 | 64,48 | >800 | − | − |
| 1-73 | 1020 | 66,62 | >800 | − | − |
| 1-73 | 1580 | ND,ND | >800 | − | − |
| 1-74 | 680 | 61,63 | >800 | − | − |
| 1-74 | 4170 | 68,55 | >800 | − | − |
| 1-75 | <20 | 66,70 | 800 | − | − |
| 1-75+ | <20 | 53,64 | >800 | − | − |
| 1-76 | 4280 | 68,71 | >800 | − | + |
| 1-76 | 22640 | 65,88 | >800 | − | + |
| 1-77 | <20 | ND,ND | >800 | − | + |
| 1-77+ | <20 | 53,57 | >800 | − | − |
| 1-78 | 10490 | 53,ND | >800 | − | − |
| 1-78 | 12210 | 58,65 | >800 | − | − |
| 1-79 | 5430 | 55,49 | >800 | − | − |
| 1-79 | 430 | 61,56 | >800 | − | − |
| 1-80 | 30 | 63,66 | 800 | − | − |
| 1-80+ | <20 | 54,53 | >800 | − | − |
| 1-81 | 8290 | 69,62 | >800 | − | − |
| 1-81 | 10820 | 55,56 | >800 | − | − |
| 1-82 | 3270 | 49,55 | >800 | − | − |
| 1-82+ | 660 | 47,48 | 550 | − | + |
| 1-83+ | <20 | 64,52 | >800 | − | − |
| 1-83 | <20 | 58,64 | >800 | − | − |
| 1-84 | 980 | 55,51 | >800 | − | − |
| 1-84 | 2480 | 65,49 | >800 | − | − |

Footnotes to Table 3
*Guinea pigs were used for all the peptides except 76 which was injected into rabbits. These are 2–5 month bleeds after initial injection, all others are 6 month bleeds.
+ Limiting dilution was calculated from dilution curves as the dilution at which an absorbance of 0.1 would be obtained.
**Fusion assay numbers represent the number of giant cells formed at 1:10 serum dilution. Control sera added had 50,65 giant cells; ND = not done.
Neutralization activity was performed as described in Methods and represents the quantity of p24 present in the supernatant in ng/ml.

TABLE 4

Sequence of env-coded Peptides for Different HIV-1 and HIV-2 Isolates, Corresponding to the Region Homologous to HIV-1 IIIB Peptide 1-69

| Isolate | | | | | | | | | | | |--------Peptide 1-69--------| | | | | | |
|---|---|---|---|---|---|---|---|---|---|---|---|---|---|---|---|---|---|
| BH10 | © | T | R | P | N | N | N | T | R | K | S | I | R | I | Q | R | GPG |
| HXB2 | − | − | − | − | − | − | − | − | − | − | R | − | − | − | − | − | − |
| BH8 | − | − | − | − | − | − | − | − | − | − | K | − | − | − | − | − | − |
| H3B3 | − | − | − | − | − | − | − | − | − | − | K | − | − | − | − | − | − |
| PV22 | − | − | − | − | − | − | − | − | − | − | − | − | − | − | − | − | − |
| BRU | − | − | − | − | − | − | − | − | − | − | − | − | − | − | − | − | − |
| MAL | − | − | − | − | G | − | − | − | − | R | − | . | . | − | H | F | − |
| ELI | | A | − | − | Y | Q | − | − | − | . | . | Q | − | T | P | I | − L − |
| SF2 | − | − | − | − | − | − | − | − | − | − | − | . | . | − | Y | I | − |
| NMJ2 | − | − | − | − | T | − | − | V | − | R | − | L | S | − | . | . | − |
| RF | − | − | − | − | − | − | − | − | − | − | . | . | − | T | K | − | − |
| Z6 | − | − | − | − | Y | K | − | − | − | Q | − | . | . | T | P | I | − L − |
| Z3 | − | − | − | − | G | S | D | K | K | I | − | Q | S | − | R | I | − |
| NY5 | − | − | − | − | − | − | − | K | − | G | − | A | − | . | . | − | − |
| CDC4 | − | − | − | − | − | − | H | − | − | − | − | V | T | L | . | . | − |
| HIV-2 ROD | − | K | − | − | G | − | K | I | V | K | Q | − | M | L | M | S | − H V |
| MN | − | − | − | − | − | Y | − | K | − | − | R | − | H | − | . | . | − |
| SC | − | − | − | − | − | − | − | − | T | R | − | − | H | − | . | . | − |

TABLE 4-continued

Sequence of env-coded Peptides for Different HIV-1 and HIV-2 Isolates, Corresponding to the Region Homologous to HIV-1 IIIB Peptide 1-69

| Isolate | |---------Peptide 1-69---------| |
|---|---|
| BH10 | R A F V T I G K I G N M . R Q A H Ⓒ |
| HXB2 | — — — — — — — — — — — — . — — — — — |
| BH8 | — — — — — — — — — — — — . — — — — — |
| H3B3 | — — — — — — — — — — — — . — — — — — |
| PV22 | — — — — — — — — — — — — . — — — — — |
| BRU | — — — — — — — — — — — — . — — — — — |
| MAL | Q — L Y — T — I V — D I . — R — Y — |
| ELI | Q S L Y — T R S R S I I I G — — — — |
| SF2 | — — — H — T — R — I G D I — K — — — |
| NMJ2 | — — — R — R E . — I G I I — — — — — |
| RF | — V I Y A T — Q — I G D I — K — — — |
| Z6 | Q — L Y — T R G R T K I I G — — — — . |
| Z3 | K V — Y A K — G — T . . . G — — — — |
| NY5 | G R T L Y A R E K I G D I — — — — — |
| CDC4 | — V W Y — T — E — L G N I — — — — — |
| HIV-2 ROD | F H S H Y Q P I N K R P . — — — W — |
| MN | — — — Y — T K N — I G T I — — — — — |
| SC | — — — Y A T — D I — — D I — — — — — |

Footnote to Table 4
HIV env aa sequences were obtained from and are fully referenced in Human Retroviruses and AIDS 1987, Los Alamos National Laboratory, Los Alamos, NM. HIV env-coded amino acid sequences are aligned for homology using standard computer programs available from, for example, IntelliGenetics, Inc., Mountain View, CA, or Genetics Computer Group, University of Wisconsin Biotechnology Center, Madison, WI.
A dash (—) indicates that the aa at that position is identical to the corresponding aa, i.e., the aa with which it is aligned, in the BH10 sequence. A dot (.) indicates that there is a gap and no aa is present at that position. Gaps are introduced to improve the alignment of the sequence.
The sequence of HIV-1 IIIB-derived env-coded peptide 1-69 is aa number 308 to 322 (numbering system according to Human Retroviruses and AIDS 1987, Los Alamos National Laboratory). The region corresponding to HIV IIIB (BH10, HXB2, BH8, HXB3, PV22) peptide 1-69 in other HIV isolates is found within a 15 to 25 aa sequence positioned approximately midway between two highly conserved Cys residues (circled), which correspond to aa number 296 and 331 in the HIV-1 IIIB isolate. A sequence of Gly-Pro-Gly (circled) is found in most of the env-coded regions corresponding to peptide 1-69 from different HIV isolates. The env-coded region in an HIV isolate corresponding to HIV-1 IIIB peptide 1-69 is encompassed within aa positions aligned, using the computer programs described above, with approximately aa number 304 to 326 of HIV-1 IIIB.

TABLE 5

Levels of Fusion Blocking Antibodies Elicited by Peptide 1-69

| Animal | Time (Months) After Start of Immunization | Antiserum Titer in Peptide 1-69 ELISA | Antiserum Titer of Fusion Blockage Activity |
|---|---|---|---|
| GP69A | 0 | <20 | <10 |
| | 1 | <20 | <10 |
| | 2 | 470 | <10 |
| | 3 | 4240 | <10 |
| | 4 | 2080 | <10 |
| | 5 | 3250 | 10 |
| | 6 | 5000 | 20 |
| | 7 | 3200 | 20 |
| | 8 | 5430 | 20 |
| | 9 | 9370 | |
| GP69B | 0 | <20 | <10 |
| | 1 | <20 | <10 |

TABLE 5-continued

Levels of Fusion Blocking Antibodies Elicited by Peptide 1-69

| Animal | Time (Months) After Start of Immunization | Antiserum Titer in Peptide 1-69 ELISA | Antiserum Titer of Fusion Blockage Activity |
|---|---|---|---|
| | 2 | 280 | <10 |
| | 3 | 840 | <10 |
| | 4 | 730 | <10 |
| | 5 | 1490 | 10 |
| | 6 | 970 | 20 |
| | 7 | 910 | 20 |
| | 8 | 1650 | 20 |
| | 9 | 950 | 20 |

Example 3

Preparation of Monoclonal Antibodies to Peptide 1-69

Materials and Methods

Peptides and Peptide Conjugates

Peptide 1-69, having the amino acid sequence RIQRG-PGRAFVTIGK, was obtained from Peninsula Laboratories, Belmont, Calif. 94002, as a 74% pure material. It was conjugated to hen egg white ovalbumin via glutaraldehyde [Reichlin, M., Meth. in Enzymol 70: 159–165 (1980)]. This peptide conjugate is referred to by the shortened name, oval-glut-69. (Other peptide-protein conjugates are named in a similar manner in this Example.) Peptide 1-69 was also coupled to bovine thyroglobulin (BTG) using the water soluble carbodiimide, 1-ethyl-3-(3-dimethylaminopropyl) carbodiimide (ECDI) [Goodfriend et al., Science 144: 1344–1346 (1964)]. After coupling, the conjugates were dialyzed against phosphate buffered saline (PBS) to remove any free peptide and excess coupling reagents.

In addition to peptide 1-69, an HIV-1 envelope-derived synthetic peptide (designated peptide #5), with the sequence MRDNWRSELYKY, amino acid numbers 475–486, was included as a control peptide. A MAb to peptide #5 which also reacts with HIV-1 gp120 has been described previously [Durda et al., AIDS Research and Human Retroviruses 4:331–342 (1988)].

Immunization and Antibody Production

Balb/cxC57 Bl/6 F1 mice (8 weeks of age), animals #5020–5029, were immunized by a procedure described by French et al.[Immunology Today 7: 344–346 (1986)]. Briefly, a single intraperitoneal inoculation of 100 μg of oval-glut-69 conjugate mixed 1:1 with complete Freund's adjuvant was given. Four weeks later, mice were bled and peptide-specific antibody responses were evaluated. The mice were rested until drops in their Ab titers were observed, at which point they were boosted with 100 μg of oval-glut-69-conjugate in incomplete Freund's adjuvant. In a like manner, animals #5040–5049 were immunized and boosted with BTG-ECDI-69. Four days after receiving the booster dose of conjugate, mice were sacrificed and their splenocytes were fused with SP 2/0-Ag 14 myeloma cells (ATCC #CRL 1581) in a typical hybridoma fusion procedure [Galfre et al., Nature 277:131–133 (1979)]. Other suitable fusion partners include P3/NS1/1-Ag4-1 (ATCC #TIB 18); P3X63Ag8U.1 (ATCC #CRL 1597); and P3X63Ag8.653 (ATCC #CRL 1580).

Following selection of the hybrids of interest by solid phase ELISA and Western blot, hybridomas were cloned twice by limited dilution (1 cell per 3 wells). Bulk antibody was produced as ascites in Balb/cxC57Bl/6 F1 mice. Ascitic fluids were purified by ammonium sulfate precipitation and protein A affinity chromatography [Ey et al., Immunochemistry 15: 429–436(1978)]. The immunoglobulins were typed as IgG1, except for MAb #5025,29.1.1.1 and #5023,24.5, which are IgG2b.

Solid Phase Enzyme Linked Immunosorbent Assay (ELISA)

Protein peptide conjugates (100 ng/well) such as those described above, e.g., BTG-ECDI-69) were adsorbed to Immulon® II microtiter plates (Dynatech Laboratories, Inc., Chantilly, Va. 22021) in 0.1M $NaCO_3$ buffer pH 9.6 at 4° C. for 18 hours [Voller et al., Manual of Clin. Immun. 69:506–510 (1976)]. The plates were then washed with 0.05% Tween® 20 in PBS (phosphate buffered saline). Hybridomas were tested for production of antibodies binding to peptide conjugate plates as described in Durda et al., AIDS Research and Human Retroviruses 4:331–342 (1988), the teaching of which is incorporated herein by reference.

Electrophoresis and Western Immunoblotting

HTLV-IIIB (as a lysate in 1% Triton® X-100) was obtained from E. I. du Pont de Nemours, Wilmington, Del. at a concentration of 800 μg/ml of protein. The lysate was disrupted with sample buffer containing 5% 2-mercaptoethanol at 100° C. for 5 minutes [Laemmli, Nature 277:680–685 (1970)] and electrophoresed on a 5–15% acrylamide gradient gel (10 cm×12 cm×0.15 cm). $^{125}I$ labeled protein molecular weight markers (Du Pont/NEN Research Products) were included in the sample. Viral proteins were electro-transblotted to nitrocellulose and Western blots were performed essentially as described by Tsang et. al. [Meth. in Enzymol. 92:377–391 (1983)]. As a diluent buffer for immunoblotting we used 5% nonfat dry milk containing 4% normal goat serum in PBS.

Inhibition of Western Blotting Activity

Peptides 1-69 and #5, previously described, were diluted in the Western blot diluent to 10 μg/ml, as were the purified MAbs. Antibody and peptides were combined 1:1 and allowed to incubate 1 hr. at 22° C. They were then assayed in the Western blot format described above.

Immunofluorescence Assay

HTLV-IIIB infected and uninfected H9 cells, provided by Roy Byington of the Infectious Disease Laboratory of the Massachusetts General Hospital, were rehydrated in PBS containing 1% bovine serum albumin (PBS BSA) at 22° C. for 1 hour. Slides were then incubated with the primary antibody as a diluted ascites or hybridoma supernatant for 2 hrs. at 22° C. After extensive washing, fluoresceinated GAM F (ab')$_2$ (Du Pont/NEN Research Products) was used to detect the presence of mouse antibodies. After 1 hour at room temperature, the fluoresceinated Ab was removed. The cells were then washed and mounted in 50% glycerol:PBS (v/v). Slides were examined with a fluorescent microscope.

Neutralization Assay

The antibody was assayed for its ability to neutralize HIV-1 infectivity in vitro, essentially according to the procedure described in D. Ho et al. [J. Virol. 61: 2024–2028 (1987)], the teaching of which is incorporated herein by reference. Hybridoma cell supernatant (35 μg/ml IgG1) was prediluted in RPMI-1640 medium containing 20% fetal calf serum (two fold serial dilutions). 100 μl of diluted antibody was added to an equal volume of purified virus equal to 50 TCID-50 units, incubated for one hour at 37° C., and added to 1.5–2.0×10$^6$ H9 cells. Cultures were incubated for 7 days at 37° C. refed, and incubated for an additional 7 days. At this time, flasks were examined for cytopathic effects with syncytia formation, and the amount of p24 HIV gag antigen present in the culture as compared to a control culture. A decrease of >90% in p24 amount was required for an antibody to be considered positive for neutralizing activity.

Inhibition of Cell Fusion

The cell fusion assay has been described by T. Matthews et al. [*Proc. Natl. Acad. Sci. USA* 84, 5424–5428 (1987)], the teaching of which is incorporated herein by reference. Briefly, 4000 infected cells (HIV-1 IIIB in CEM cells and HIV-1 HAT3 in H9 cells) in 30 μl are seeded into microtiter wells. 30 μl of diluted antibody (as described above) are added. After 30 min. at 37° C., 30 μl containing 56,000 SupT-1 cells in RPMI media are added to the wells. The plates are incubated overnight at 37° C. and evaluated for syncytia formation (cell fusion) in the morning. Wells without antibody have between 50 and 70 syncytia per well.

RESULTS

MAb Fine Specificities

Figure 2:
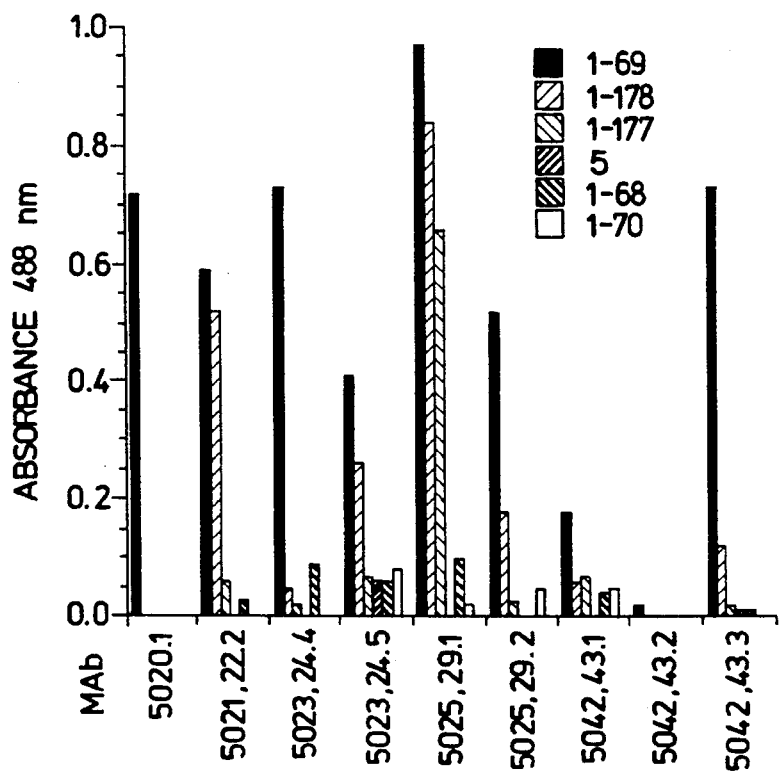

The MAbs to peptide 1-69 (HIV-1 IIIB envelope aa#308–322) were tested for immunoreactivity to the immunizing peptide, 1-69, as well as other overlapping peptides from the amino acid 298-332 region and on various smaller peptides from within the 308–322 region. The sequences of the peptides employed and their relative positions are shown in Table 6. As can be seen in FIG. 2, the MAbs were specific for the immunizing peptide. Note in FIG. 2 that none of the MAbs shown there except #5023,24.5 reacted with peptide #5, the control peptide representing HIV-1 envelope amino acids 475-486, nor did they react significantly with peptides #1-68 and 1-70, which overlap peptide 1-69 on the amino and carboxyl ends respectively. Varying degrees of reactivity are observed with peptides 1-177 and 1-178, which cover a smaller portion of env aa's 308–322 than does peptide 1-69.

The solid phase ELISAs employed in the experiment used free peptides coated onto ELISA microtiter plates. MAbs in FIG. 2 and Table 7 are referred to by shortened clone designations. Unabridged clone numbers are as follows: 5021,22.2=5021,22.2.1.1; 5023,24.4=5023,24.4.1.1; 5025,29.1=5025,29.1.1.1; 5025,29.2=5025,29.2.1.1; and 5042,43.3=5042,43.3.2.1. The latter were used for deposit with the ATCC.

The specificities of the MAbs were also examined by solution phase inhibition. In these experiments MAbs were preincubated with free peptide prior to being titrated in an ELISA with peptide 1-69 coated plates. A summary of the results from those experiments is presented in Table 7.

TABLE 6

| Peptide # | Sequence |
| --- | --- |
| 1–68 | RPNNNTRKSIRIQRG |
| 1–69 | RIQRGPGRAFVTIGK |
| 1–70 | VTIGKIGNMRQAHCNI |
| 1–177 | GPGRAFVTIG |
| 1–178 | QRGPGRAFV |
| 5 | MRDNWRSELYKY(not part of above set of peptides) |

TABLE 7

| | Peptide Designation and Sequence | HIV-1 Isolate |
| --- | --- | --- |
| 1-68 | RPNNNTRKSIRIQRG | BH10 |
| 1-69 | RIQRGPGRAFVTIGK | BH10 |
| 1-70 | VTIGKIGNMRQAHCNI | BH10 |
| 1-169 | TKGPGRVIYATGQIIG | RF |
| 1-170 | HIGPGRAFYTTKNIIG | MN |
| 1-171 | KRKRIHIGPGRAFYTT | MN |
| 1-175 | RIQRGPGRA | BH10 |
| 1-176 | AFVTIGK | BH10 |
| 1-177 | GPGRAFVTIG | BH10 |
| 1-178 | QRGPGRAFV | BH10 |

| | Peptide Used to Inhibit | | | | | | | | |
| --- | --- | --- | --- | --- | --- | --- | --- | --- | --- |
| MAb | 1–68 | 1–69 | 1–70 | 1–169 | 1–170 | 1–171 | 1–175 | 1–177 | 1–178 |
| 4407.2 | ++ | − | ND | ND | ND | ND | − | ND | ND |
| 5021,22.2 | − | ++ | − | − | +/− | +/− | ++ | − | ND |
| 5023,24.4 | − | +++ | − | +/− | + | − | − | ++ | + |
| 5025,29.1 | − | ++ | − | − | ++ | +/− | − | ++ | + |
| 5025,29.2 | − | +++ | − | +/− | ++ | + | ++ | − | ++ |
| 5042,43.3 | − | ++ | − | − | − | − | ++ | − | ND |

Pluses (+) indicated level of inhibition: +/− indicates >20% inhibition at 1 mg/ml of free, soluble peptide, + indicates >90% inhibition at 100 μg/ml, ++ >90% at 10 μg/ml, and +++ >90% at 1 μg/ml.
Antibody concentrations were variable but on the order of 100 ng/ml.
Antibody was premixed with varying concentrations of peptide in PBS:BSA (1:1). After ~1 hour at 23° C. 100 μl of the mixture was added to an Immulon II plate coated with either 1–68 or 1–69 at 25 ng/50 μl/well which had been blocked with PBS:BSA. Incubation with the MAb on the plate was for ~60 min at 23° C.
All MAbs were nonreactive with 1–176 and 1–70. MAb 4407.2 was made to peptide 1–68.

To determine the reactivities of the MAbs with viral components, Western blots were performed under a variety of conditions. Viral lysates (200 μg of protein per gel) were disrupted in the presence or absence of 2-mercaptoethanol and separated by SDS-PAGE. The Western blot reactivities of the MAbs shown in FIG. 2 with reduced viral components and with components of a mock viral lysate (uninfected H9 cells processed like virus), as described in Durda et al., supra, were determined. All of the MAbs, except #5020.1; 5023,24.5; 5042,43.1; and 5042,43.2, were found to react with an HIV-1 viral component of ~120 kD under reducing and nonreducing conditions. No reactivity was observed when the MAbs were tested with protein components from a mock virus preparation. As a specificity control for antibody, an IgG1MAb, #2085.1, which does not recognize any viral components was employed. This control MAb fails to react with any HIV-1 viral components.

To confirm that the Western blot signal generated by the strongest of these MAbs, MAb 5023,24.4.1.1, is due to the amino acid sequence, RIQRGPGRAFVTIGK, we tested the MAb in the presence or absence of 1-69. Inhibition of the blotting signal was seen with the cognate peptide, 1-69, but not with a control peptide, #5.

In immunofluorescence with fixed cells on slides, MAb 5023,24.4.1.1, as well as MAbs 5021,22.2.1.1, 5025,29.1.1.1 and 5042,43.3.2.1, showed positive reactivity on H9 cells infected with the IIIB isolate of HIV-1. The MAbs were then tested on live HIV-1 IIIB infected CEM/NKR cells using a fluorescence activated cell sorter. MAb 5023,24.4.1.1 reacted with 47% of HIV-1 IIIB infected cells; only 5% of cells infected with the HIV-1 MN isolate appeared to be stained by 5023,24.4.1.1. No reactivity was observed with cells infected with the HIV-1RF isolate or with uninfected CEM/NKR cells. MAb 5025,29.1.1.1 showed a similar reactivity pattern but with a lower % of HIV-1 IIIB infected cells staining (27%) and a higher % of HIV-1 MN (16%) cells staining. Control class matched antibodies (myeloma proteins), on the other hand, showed no significant binding to either live infected or uninfected cells. This suggests that there may be some degree of cross reactivity with strains of HIV other than IIIB, but no significant reactivity with noninfected cells.

Virus Neutralization

When tested for neutralizing activity and compared with other MAbs and antisera the results shown in Table 8 were obtained. MAb 5023,24.4.1.1 showed the strongest HIV-1 neutralizing activity, which in this particular assay format is as strong as that seen with most human neutralizing sera. MAb 5021,22.2.1.1 also demonstrated HIV-13B neutralizing activity, as shown in Table 8.

TABLE 8

Neutralization of HTLV-3B by MAbs to Peptide 1-69

| Antibody | Neutralization Titer |
| --- | --- |
| 5023,24.4.1.1 | 64 |
| 5021,22.2.1.1 | 16–32 |
| MOPC 21 (IgG1 control) | <8 |
| negative serum | <4 |
| | (3 – 4 + CPE at 1:4) |
| positive serum | >4 |
| | (0 CPE at 1:4) |

Note that the serum samples are well defined human sera and that the positive serum has a titer of 1/32 to 1/64 in neutralization when tested in a titration format. CPE refers to the cytopathic effect (e.g. syncytia formation and cell death) induced in the host cells by replicating HIV-1. It is scored visually with 3 – 4 + being the most severe cell destruction due to active HIV-1.

Cell Fusion Blocking

The data demonstrating the inhibition of fusion of HIV-1 infected cells with target cells, SupT-1, (obtained from D. Bolognesi, Duke University) by MAbs 5021,22.2.1.1, 5023, 24.4.1.1, 5025,29.1.1.1 and 5042, 43.3.2.1 are presented in Table 9. Note that SupT-1 is a high expresser of the CD4 antigen which is the receptor of HIV-1 on T cells. Activity against HIV-1 III B and HIV-1MN infected cells was evaluated. It is notable that MAb 5025,29.1.1.1 exhibits fusion-blocking activity not only against the HIV-1 IIIB isolated from which the antigen was derived, but also against the HIV-1 MN isolate Previous reports suggest that such HIV-inhibiting antibodies are type or isolate specific.

TABLE 9

Inhibition of Syncytia Formation (Fusion) by MAbs to Peptide 1-69

| | # syncytia/well | |
| --- | --- | --- |
| MAb# | HIV-1 3B | HIV-1 MN |
| 4407.2 | 58 | 61 |
| 5021,22.2.1.1 | 3 | 54 |
| 5023,24.4.1.1 | 0 | 40 |
| 5025,29.1.1.1 | 2 | 14 |
| 5042,43.3.2.1 | 0 | 56 |
| 2085.1 (IgG1 control) | 69 | 49 |
| 351–56 (2b control) | 52 | 53 |
| cells with no MAb | 76 | 64 |

All MAbs were ascites and were tested at a 1/50 dilution. Note that MAb 4407.2 was made to peptide 1–68; MAb 351–56 is an anti-Hras MAb; MAb 2085.1 was made to aa's 740–750 of the HIV-1 (3B) envelope protein. MAb 2085.1 has demonstrated no reactivity with envelope or any other viral components. Other IgG1 and IgG2b controls would be expected to yield comparable results.

The fact that MAb 5021,22.2.1.1 reacts with peptide 1-178 (FIG. 2) and is blocked by peptide 1-175 (Table 7) indicates that the epitope recognized by 5021.22.2.1.1 is contained within the sequence QRGPGRA, common to both peptides 1-178 and 1-175.

The fact that MAb 5025,29.1.1.1 reacts with peptide 1-177 and 1-178 (FIG. 2 and Table 7) indicates that the epitope recognized by 5025,29.1.1.1 is contained within the sequence GPGRAFV, which is common to both peptides.

The finding that MAb 5042,43.3.2.1 is blocked by peptide 1-175 (Table 7) indicates that the epitope recognized by MAb 5042,43.3.2.1 is contained within the sequence RIQRGPGRA.

The finding that MAb 5023,24.4.1.1 is blocked by peptide 1-177 (Table 7) indicates that this MAb recognizes an epitope formed by the sequence GPGRAFTIG The results taken together indicate that the critical epitope recognized by antibodies with virus-inhibiting activity is formed by residues GPGRA.

Interestingly, MAb 5025, 29.1.1.1 inhibits HIV-1 3B as well as HIV-1 MN (Table 9). Thus, 5025, 29.1.1.1 recognizes an epitope formed by the sequence GPGRAFV, as discussed above, but also the corresponding sequence from HIV-1 MN which is GPGRAFY (Table 4). On the basis of the sequence in the peptide 1-69 region, it is expected that MAb 5025, 29.1.1.1 would also inhibit HIV-1 strains SF2 and NMJ2 (Table 4).

Peptides of 5 to 10 amino acids comprising the epitopes QRGPGRA, RIQRGPGRA, GPGRAFVTIG, GPGRAFV, and GPGRA, would be useful immunogens, when conjugated to an immunologically acceptable carrier, for inducing the production of HIV-inhibiting antibodies in a mammal. Similarly, the corresponding peptides from other HIV isolates would also be expected to be useful immunogens for inducing the production of HIV-inhibiting antibodies in a mammal.

It is interesting and unexpected to observe that a single MAb to peptide 1-69 may exhibit strong HIV-1 neutralizing and fusion-blocking activity. Such MAbs are expected to have significant therapeutic utility.

Hybridoma cells lines, designated #5021,22.2.1.1, 5023, 24.4.1.1, 5025,29.1.1.1, 5025,29.2.1.1., and 5042,43.3.2.1, were deposited on Mar. 1, 1989in the American Type Culture Collection (ATCC), Rockville, Md., in accordance with the provisions of MPEP 608.01(p)(C)(1)(2) and (3) and the Budapest Treaty. ATCC accession numbers for these hybridoma cell lines are HB10040, HB10043, HB10041, HB10042, and HB10044, respectively. Access to the cultures will be available during pendency of the patent application to one determined by the Commissioner to be entitled thereto under 37 CFR 1.14 and 35 USC 122. Upon granting of a patent all restrictions on the availability of the culture to the public will be irrevocably removed.

As used herein, "consisting essentially of" is intended to have its customary meaning; namely, that all specified materials and conditions are very important in practicing the invention but that additional unspecified materials and conditions, including other therapeutic agents or ingredients, are not excluded so long as they do not prevent the benefits of the invention from being realized.

We claim:

1. A chemically synthesized peptide selected from the group consisting of:

a peptide characterized by the amino acid sequence RIQRGPGRAFVTIGK;

a peptide characterized by the amino acid sequence IHFGPGQALYTTGI;

a peptide characterized by the amino acid sequence RTPIGLGQSLYTTRS;

a peptide characterized by the amino acid sequence IYIGPGRAFHTTGR;

a peptide characterized by the amino acid sequence SIGPGRAFRTRE;

a peptide characterized by the amino acid sequence ITKGPGRVIYATGQ;

a peptide characterized by the amino acid sequence TPIGLGQALYTTRG;

a peptide characterized by the amino acid sequence SIRIGPGKVFYAKGG;

a peptide characterized by the amino acid sequence AIGPGGRTLYARE;

a peptide characterized by the amino acid sequence TLGPGRVWYTTGE;

a peptide characterized by the amino acid sequence MLMSGHVFHSHYQPI;

a peptide characterized by the amino acid sequence HIGPGRAFYTTKN;

a peptide characterized by the amino acid sequence HIGPGRAFYATGD.

2. A chemically synthesized peptide characterized by the amino acid sequence RIQRGPGRAFVTIGK.

3. A chemically synthesized peptide characterized by the amino acid sequence HIGPGRAFYTTKN.

4. A chemically synthesized peptide characterized by the amino acid sequence HIGPGRAFYATGD.

* * * * *